United States Patent
Varineau et al.

(10) Patent No.: US 8,334,323 B2
(45) Date of Patent: *Dec. 18, 2012

(54) ALKYLENE OXIDE-CAPPED SECONDARY ALCOHOL ALKOXYLATES USEFUL AS SURFACTANTS

(75) Inventors: Pierre T. Varineau, Lake Jackson, TX (US); Wanglin Yu, Midland, MI (US); Kara S. Weber, Lake Jackson, TX (US); Cynthia L. Rand, Sanford, MI (US)

(73) Assignee: Dow Global Technologies LLC, Midland, MI (US)

( * ) Notice: Subject to any disclaimer, the term of this patent is extended or adjusted under 35 U.S.C. 154(b) by 88 days.

This patent is subject to a terminal disclaimer.

(21) Appl. No.: 12/808,936

(22) PCT Filed: Dec. 23, 2008

(86) PCT No.: PCT/US2008/088188
§ 371 (c)(1),
(2), (4) Date: Jun. 17, 2010

(87) PCT Pub. No.: WO2009/088778
PCT Pub. Date: Jul. 16, 2009

(65) Prior Publication Data
US 2010/0267844 A1 Oct. 21, 2010

Related U.S. Application Data

(60) Provisional application No. 61/020,416, filed on Jan. 11, 2008.

(51) Int. Cl.
*C07C 43/13* (2006.01)
*C07C 41/01* (2006.01)
*C11D 1/722* (2006.01)
*C08K 5/06* (2006.01)
*A61K 47/08* (2006.01)
*C09D 7/12* (2006.01)
*C09D 11/02* (2006.01)
*C09K 8/60* (2006.01)
*C10M 105/18* (2006.01)
*D21H 17/06* (2006.01)
*A61P 43/00* (2006.01)

(52) U.S. Cl. ........ 514/772; 568/618; 568/620; 568/622; 510/506; 524/376; 106/287.26; 106/31.13; 507/261; 508/579; 162/158

(58) Field of Classification Search .................. None
See application file for complete search history.

(56) References Cited

U.S. PATENT DOCUMENTS

| | | |
|---|---|---|
| 3,359,331 A | 12/1967 | Baker et al. |
| 3,539,519 A | 11/1970 | Weimer |
| 4,152,592 A | 5/1979 | Molina |
| 4,340,766 A | 7/1982 | Klahr et al. |
| 4,753,885 A | 6/1988 | Dietsche et al. |
| 4,836,951 A | 6/1989 | Totten et al. |
| 4,898,621 A | 2/1990 | Pruehs et al. |
| 4,927,954 A | 5/1990 | Knopf et al. |
| 4,942,049 A | 7/1990 | Schmid et al. |
| 5,525,702 A | 6/1996 | Nace |
| 5,576,281 A | 11/1996 | Bunch et al. |
| 5,766,371 A | 6/1998 | Bunch et al. |
| 5,912,209 A | 6/1999 | Kassebaum et al. |
| 6,057,375 A | 5/2000 | Wollenweber et al. |
| 6,680,412 B2 | 1/2004 | Gumbel et al. |
| 6,693,065 B2 | 2/2004 | Gentilhomme et al. |
| 2005/0014979 A1 | 1/2005 | Eleveld et al. |
| 2005/0170991 A1 | 8/2005 | Ruland et al. |
| 2006/0069220 A1 | 3/2006 | Meurs et al. |
| 2007/0275122 A1 | 11/2007 | Cazaroto et al. |
| 2010/0075389 A1 | 3/2010 | Wurm et al. |

FOREIGN PATENT DOCUMENTS

| | | |
|---|---|---|
| EP | 0389157 | 9/1990 |
| EP | 0850907 B1 | 9/2004 |
| EP | 1454667 | 9/2004 |
| GB | 899222 | 6/1962 |
| JP | 10192685 | 7/1998 |
| WO | 9612001 | 4/1996 |
| WO | 0141909 | 6/2001 |
| WO | 2005039732 | 5/2005 |

OTHER PUBLICATIONS

Rakutani et al., "Secondary Alcohol Ethoxylates", Annual Surfactants Review, 1999, vol. 2, pp. 216-247.
XP002522729, abstract for JP11323753, dated Nov. 1999.
XP002522671, abstract for JP3131698, dated Jun. 1991.
J.H. McFarland, et al., Performance and Properties of Nonionic Surfactants from Linear Secondary Alcohols, 1964, Union Carbide Chemicals Division, Research and Development Department, vol. 41, pp. 742-746.
W.B. Satkowski, et al., Polyoxyethylene Alcohols, Nonionic Surfactants, Monsanto Company, Inorganic Chemicals Division, 1967, Ch. 4, pp. 86-93.
N. Kurata, et al., Secondary Alcohol Ethoxylates, American Chemical Society, 1981, pp. 113-157.

*Primary Examiner* — Rosalynd Keys

(57) ABSTRACT

Disclosed are compositions of the formula wherein $R^1$ and $R^2$ are each independently hydrogen or a linear or branched alkyl group containing from (1) to about (18) carbon atoms, provided that $R^1$ and $R^2$ together contain from about (8) to about (18) carbon atoms, and further provided that less than about 10 mole percent of $R^1$ or $R^2$ is hydrogen; $R^3$ is hydrogen or an alkyl radical containing from (1) to about (6) carbon atoms; $R^4$ and $R^5$ are each independently hydrogen or an alkyl radical containing from (2) to about (6) carbon atoms, provided that $R^4$ and $R^5$ together contain from (2) to about (6) carbon atoms; m is an average value ranging from (0) to about (10), and n is an average value ranging from about (3) to (about 40), provided that the group containing m and the group containing n may be exchanged with one another as to position; and z is an average value ranging from about (0.5) to about (5). These compositions are conveniently prepared by a process including at least two steps and are useful as surfactants.

15 Claims, 1 Drawing Sheet

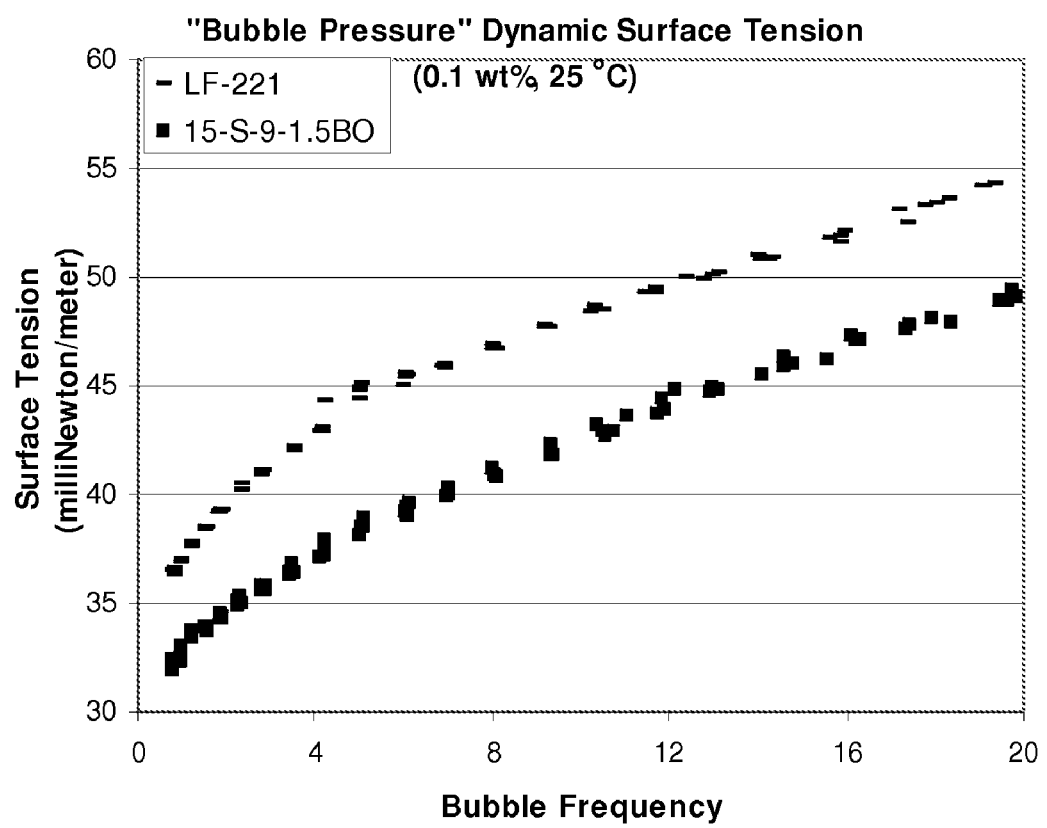

ALKYLENE OXIDE-CAPPED SECONDARY ALCOHOL ALKOXYLATES USEFUL AS SURFACTANTS

CROSS REFERENCE TO PRIOR RELATED APPLICATIONS

This is a §371 application of PCT International Patent Application Number PCT/U.S.2008/088188 filed Dec. 23, 2008, and claims the benefit of U.S. Provisional Application No. 61/020,416 filed Jan. 11, 2008, each of which is incorporated herein by reference in its entirety.

BACKGROUND OF THE INVENTION

1. Technical Field

This invention relates to the field of surfactants. More particularly, it relates to compositions and methods of preparing novel alkylene oxide capped alkoxylates.

2. Background of the Art

Surfactants are used in the chemical and manufacturing industries for a wide variety of purposes. These include, for example, imparting or enhancing wettability and detergency in products including wetting agents, emulsifiers, rinse aids, defoam/low foam agents, spray cleaning agents, drug delivery agents, emulsifiers for herbicides and pesticides, metal cleaning agents, paints, coatings, agricultural spread and crop growth agents, stabilizing agents for latexes, paints, and paper products, and the like. One group of frequently-employed surfactants is the nonionic surfactants, and in particular, alkylene oxide capped nonionic surfactants. These capped nonionic surfactants tend to generate less foam than uncapped nonionic surfactants, making many of them useful in applications where low foam is critical, such as in mechanical washing processes, and in paint and coating products.

Unfortunately, some alkylene oxide capped nonionic surfactants exhibit poor or otherwise unacceptable biodegradability. Examples of approaches to this problem include that disclosed in U.S. Pat. No. 5,576,281 to Bunch et al., which describes an epoxy capped poly(oxyalkylated) alcohol composition represented by the formula:

$$R^1O[(CH_2CHCH_3)O]_x(CH_2CH_2O)_y[CH_2CH(OH)R^2]$$

wherein $R^1$ is a linear, aliphatic hydrocarbon radical having from about 4 to about 18 carbon atoms including mixtures thereof; $R^2$ is a linear, aliphatic hydrocarbon radical having from about 2 to about 26 carbon atoms including mixtures thereof; x is an integer having a value from 1 to about 3; and y is an integer having a value from 5 to about 30. This composition is used in an automatic dishwasher composition or cleaning composition.

Another example of an epoxy-capped poly(oxyalkylated) alcohol is described in U.S. Pat. No. 5,766,371, also to Bunch et al., wherein the formula is shown as:

$$R^1O[(CH_2CH(CH_3))O]_x(CH_2CH_2O)_y[CH_2CH(OH)R^2]_z$$

wherein $R^1$, $R^2$, x and y are as defined in the previous paragraph; and z is an integer having a value of from 1 about 3. Again, this epoxy-capped poly(oxyalkylated) alcohol is shown as being particularly useful in an automatic dishwasher composition.

Yet another example of an epoxy capped poly(alkoxylated) alcohol is described in U.S. Pat. No. 4,898,621, to Pruehs et al., wherein the formula is shown as:

$$R^1—(CHOH)(CHR^3)(OCH_2CH_2)_nOR^2$$

wherein $R^1$ is hydrogen or a linear C1-C16 alkyl radical; $R^2$ is a linear or branched C4-C8 alkyl radical; $R^3$ is a hydrogen or C1-C16 alkyl radical; and n is a number between 7 to 30, with the proviso that the total number of carbon atoms in $R^1$ and $R^3$ is 6 to 16.

Another example of an alkylene oxide capped poly (alkoxylate) is described in WO9612001 to Groom et al., wherein the formula is shown as $$R^3O[CH_2CH(CH_3)O]_x(CH_2CHR^4O)_y[CH_2CH(OH)R^5]_z$$

wherein $R^3$ is a linear, aliphatic hydrocarbon radical having an average of from about 4 to about 18 carbon atoms, including mixtures thereof; $R^4$ is hydrogen or a lower alkyl having between 1 and 6 carbon atoms; and $R^5$ is a linear, aliphatic hydrocarbon radical having an average of from about 2 to 14 carbon atoms, including mixtures thereof; x is zero or an integer having a value from 1 to about 5; y is an integer having a value from 1 to about 30; and z is an integer having a value of from 1 to about 3.

Still another example of an alkylene oxide capped poly (alkoxylate) is described in U.S. Pat. No. 4,340,766 to Klahr et al., wherein the formula is shown as:

$$R^1O—(CH_2CH_2O)_n(CH_2CH(C_2H_5)O)_m—H$$

wherein $R^1$—O is an alkanol with 8 to 20 carbon atoms; n has any value from 4 to 14; and m is a real number with values ranging from 1.6 to 2.4.

Yet another example of an alkylene oxide capped poly (alkoxylate) is described in U.S. Pat. No. 3,539,519 to Weimer wherein the formula is shown as:

$$R^1O—(CH_2CH_2O)_n(CH_2CH(C_2H_5)O)_m—H$$

wherein $R^1$—O is an alkanol with 8 to 18 carbon atoms; n has any value from 3.5 to 10; and m is a real number with values ranging from 0.5 to 1.5.

Another example of an alkylene oxide capped poly (alkoxylate) is described in U.S. Pat. No. 6,693,065 to Gentilhomme et al., wherein a surfactant of the following formula is a component of a detergent composition:

$$R^1O—(CH_2CH_2O)_n(CH_2CH(R^2)O)_m—H$$

wherein $R^1$ is an alkyl chain with 8 to 20 carbon atoms; $R^2$ is an alkyl radical containing 1 or 2 carbon atoms; n has any value from 8 to 15; and m is a real number with values ranging from 1 to 10.

Yet another example of an alkylene oxide capped poly (alkoxylate) is described in JP10192685 to Tatsuo et al., wherein the formula is shown as:

$$RO(AO)_m(BO)_nH$$

wherein R is a hydrocarbon group with a carbon number of 8 or 9 that has one or more side chains; AO is an oxyalkylene radical with carbon numbers of 2-3; BO expresses an octybutylene radical; m is 6-26; and n is from 1 to 3.

Although the above compositions represent low foaming surfactants with some biodegradability, the performance of the above compositions lack desirable performance attributes such as rapid dynamic surface tension reduction, which in many cases is critical for effective cleaning.

The prior art also has examples of alcohol alkoxylates based on secondary alcohols. For example, secondary alcohol poly(alkoxylates) are described in U.S. Pat. No. 5,912,209 to Kassebaum, wherein the formula is shown as:

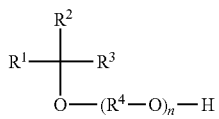

wherein $R^1$ and $R^2$ are independently straight or branched chain C2 to about C28 alkyl, aryl or alkylaryl groups and the total number of carbon atoms in $R^1$ and $R^2$ is about 7 to about 30; $R^3$ is hydrogen; $R^4$ groups are independently C1 to C4 alkylene groups; and n is an average number from about 3 to about 30.

Another example of a secondary alcohol alkoxylate is shown in European Patent 0 850 907 to Kadono et al., wherein the formula is shown as:

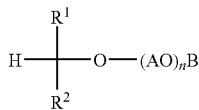

wherein $R^1$ and $R^2$ represent an alkyl group, provided that the total number of carbon atoms of $R^1$ and $R^2$ is in the range of 7 to 29 and the number of carbon atoms of $R^2$ is not less than that of $R^1$; A represents a lower alkylene group; n represents a numeral in the range of 1 to 50 on the average, provided that when n is not less than 2, the number of species of oxyalkylene group represented by AO may be either one or two or more, and that when the oxyalkyl groups have two or more species, all the oxyalkylene groups are present in the average of n; and b represents a hydrogen atom or $SO_3M$ (wherein M represents an alkali metal atom, an alkaline earth metal atom, an ammonium group or a substituted ammonium group), wherein the composition comprises from 30 to 90 mole percent of the higher secondary alcohol alkoxylate compound (X) having a methyl group for $R^1$ and 70 to 10 mole percent of the higher secondary alcohol alkoxylate compound (Y) having an alkyl group of 2 or more carbon atoms for $R^1$.

Despite the diversity of nonionic surfactant inventions as described hereinabove and in the art in general, biodegradability, dynamic surface tension reduction, and optimal performance have, for certain applications, heretofore remained elusive.

SUMMARY OF THE INVENTION

The present invention provides, in one aspect, alcohol alkoxylates with an improved spectrum of properties, which may be used, in particular, as low foam surfactants. These are secondary alcohol alkoxylates of the formula

FORMULA 1

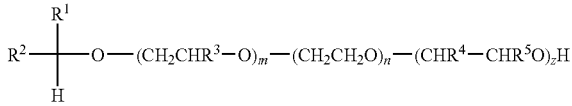

wherein $R^1$ and $R^2$ are each independently hydrogen or a linear or branched alkyl $R^2$ group containing from 1 to about 18 carbon atoms, provided that $R^1$ and $R^2$ together contain from about 8 to about 18 carbon atoms, and further provided that less than about 10 mole percent of $R^1$ or $R^2$ is hydrogen; $R^3$ is hydrogen or an alkyl radical containing from 1 to about 6 carbon atoms; $R^4$ and $R^5$ are each independently hydrogen or an alkyl radical containing from 2 to about 6 carbon atoms, provided that $R^4$ and $R^5$ together contain from 2 to about 6 carbon atoms; m is an average value ranging from 0 to about 10, and n is an average value ranging from about 3 to about 40, provided that the group containing m and the group containing n may be exchanged with one another as to position; and z is an average value ranging from about 0.5 to about 5.

In another aspect, the present invention provides a method of preparing a surfactant composition comprising contacting a linear or branched secondary alcohol with at least one first alkylene oxide, such that an alkoxylated linear secondary alcohol is formed, and then capping the alkoxylated linear secondary alcohol with a second alkylene oxide to form the surfactant composition of Formula 1.

BRIEF DESCRIPTION OF THE DRAWING

FIG. 1 shows a plot of surface tension (ST) versus bubble frequency for PLURAFAC™ LF-221, in comparison with that for an inventive composition. Lower surface tensions at higher bubble frequencies indicate a more rapid lowering of surface tension.

DETAILED DESCRIPTION OF THE INVENTION

The compositions of the invention may be made, in many cases, in a convenient and cost-effective manner, and are useful as nonionic surfactants in a wide variety of applications. These surfactants may exhibit highly desirable properties, such as good biodegradability and, therefore, environmental acceptance in such applications. In certain embodiments these surfactants may also exhibit reduced foaming and faster dynamic surface tension reduction, when compared with some other nonionic surfactants.

The starting materials include, first, at least one linear or branched secondary alcohol. This alcohol, in some non-limiting embodiments, contains a total of from about 3 to about 18 carbon atoms, and in still other non-limiting embodiments, contains from about 8 to about 16 carbon atoms. In particularly preferred embodiments, the alkyl group may contain from about 11 to about 15 carbon atoms. It is also characterized by a linear or branched alkyl group ($R^1$ and $R^2$, independently) that may be hydrogen alone or may have from 1 to about 18 carbons, and in some non-limiting embodiments from 1 to about 15 carbons, and in yet other non-limiting embodiments, from 1 to about 14 carbons. In certain non-limiting embodiments, appropriate selections may include, for example, linear or branched isomers of the following: 2-decanol, 3-decanol, 4-decanol, 5-decanol, 2-undecanol, 3-undecanol, 4-undecanol, 5-undecanol, 2-dodecanol, 3-dodecanol, 4-dodecanol, 5-dodecanol, 6-dodecanol, 2-tridecanol, 3-tridecanol, 4-tridecanol, 5-tridecanol, 6-tridecanol, 2-tetradecanol, 3-tetradecanol, 4-tetradecanol, 5-tetradecanol, 6-tetradecanol, 7-tetradecanol, 2-pentadecanol, 3-pentadecanol, 4-pentadecanol, 5-pentadecanol, 6-pentadecanol, 7-penta-decanol, 2-hexadecanol, 3-hexadecanol, 4-hexadecanol, 5-hexadecanol, 6-hexadecanol, 7-hexadecanol, 8-hexadecanol, and combinations thereof. In other non-limiting embodiments, appropriate selections may include, for example, branched secondary alcohols such as trimethyl nonanol; methyl-, ethyl-, propyl-, butyl-, hexyl-, heptyl-, octyl-, nonyl-, and decyl-branched secondary alcohols; and combinations thereof. Other non-limiting embodiments may include the secondary alcohols derived from hydrolysis of highly branched tripropylene, tetrapropylene, dibutylene, tributylene, and dihexene, and combinations thereof. In other non-limiting embodiments the alcohol may be, for example, a linear or branched secondary alcohol produced according to methods such as those described in U.S. Pat. No. 4,927,954, the disclosure of which is incorporated herein by reference in its entirety. Up to about 10 mole percent of one or more primary alcohols having carbon chain lengths ranging from about C10 to about C16 may, in some embodiments, be included with the secondary alcohols specified above, but such inclusion is not required. Non-limiting examples of suitable primary alcohols include 1-decanol, 1-undecanol, 1-dodecanol, 1-tridecanol, 1-tetradecanol, 1-pentadecanol, and 1-hexadecanol.

Generally, these poly(oxyalkylated) alcohols may be made by first reacting the linear or branched secondary alcohol, or mixture of alcohols, having an average chain length of from about 3 to about 18 carbon atoms, with ethylene oxide, propylene oxide, butylene oxide, or a higher alkylene oxide, in either a random feed or block feed, as described in Formula 1. This reaction serves to increase the effective molecular weight of the hydrophobe by the addition of such alkylene oxides, such as ethylene oxide, propylene oxide, butylene oxide, or hexene oxide. For example, in some non-limiting embodiments the desired degree of alkoxylation, represented by the subscripts m and n in Formula 1 hereinabove, have values of m ranging from 0 to about 10, and n ranging from about 3 to about 40. In preferred embodiments, the values of m range from 0 to about 5, and n ranges from about 3 to about 20. In even more preferred embodiments, the value of m ranges from 0 to about 3, and n ranges from about 3 to about 12. It is noted that the alkoxylated portions of Formula 1, represented as the groups containing the subscripts m and n, may be in either random or block form, and may be exchanged with one another as to position.

The methods and conditions used for this first alkoxylation may be any that are known to those skilled in the art. For example, in one non-limiting embodiment, this reaction may be carried out at an elevated temperature or temperatures ranging from about 20° C. to about 180° C. In other non-limiting embodiments, the temperature may range from about 100° C. to about 160° C. Pressures from about 14 psig to about 60 psig may, in certain non-limiting embodiments, be particularly efficacious, but other pressures may also be effectively employed. Those skilled in the art will be able to determine appropriate conditions with, at most, routine experimentation. Further discussion concerning preparation of secondary alcohol alkoxylates may be found in, for example, Rakutani, et al., "Secondary alcohol ethoxylates," *Annual Surfactants Review* (1999) 2, 216-247, which is incorporated herein by reference in its entirety.

In some non-limiting embodiments the first step alkoxylation or alkoxylations (represented by the subscripts m and n in Formula 1 above) may be carried out in the presence of an effective amount of a suitable acidic catalyst, such as a boron trifluoride etherate solution, in order to increase the rate and/or yield of the reaction. Metal cyanide catalysts may alternatively be employed. The amount of the catalyst may, in such embodiments, range from about 0.005 percent to about 1 percent by weight, based on the alcohol. After the addition of from 1 to about 10 mole equivalents of alkylene oxide, the product may be neutralized with a base, such as sodium hydroxide, and then purified via distillation to remove unreacted alcohol and residual catalyst. Further alkoxylation (represented by the subscripts m and n in Formula 1 above) may be carried out in the presence of an effective amount of acid or base catalysts, such as those discussed in "Nonionic Surfactants", Martin, J. Schick, Editor, 1967, Marcel Dekker, Inc., and United States Patent Application Publication (USPAP) 2005/0170991A1, which are incorporated herein by reference in their entireties. Those skilled in the art will understand that the number of alkoxylations that may be done to obtain a satisfactory molecular weight, prior to capping, is not critical to the invention. In general, a satisfactory molecular weight may, in some embodiments, range from about 300 to about 1400.

In a second or final step, the product of the alkoxylation, or alkoxylations, as described hereinabove, may be capped with a second alkoxylene oxide, using known alkoxylation techniques. The capped portion of the molecule represented by Formula 1 hereinabove is represented as the group containing the subscript z. For this final capping alkoxylation, an alkylene oxide that is either the same as or different from that used for the first step alkoxylation may be employed. For example, alkylene oxides selected from butylene oxide, pentene oxide, hexene oxide, heptene oxide, or octene oxide, or any combination thereof, may be effectively employed. The amount of alkylene oxide used for the capping may range from about 0.5 to about 5 times stoichiometric, and in certain particular embodiments, it may range from about 0.5 to about 3.5, or from about 1 to about 3, times stoichiometric. While a variety of alkylene oxides is suitable for use in this second step alkoxylation, in certain non-limiting embodiments butylene oxide may be particularly efficacious. One advantage of using butylene oxide, rather than, for example, a lower alkylene oxide such as propylene oxide for this capping is that a reduced molar amount of butylene oxide serves to comparably suppress foam and reduce the cloud point of the composition. Therefore, the end product may be more biodegradable and less expensive to produce than surfactants based on lower alkylene oxide capping. Another advantage is that the use of butylene oxide, pentene oxide, hexene oxide, heptene oxide, octene oxide, or combinations thereof, as capping agents, instead of a lower alkylene oxide, significantly reduces the reactivity of the resulting surfactants toward reagents, such as isocyanates, that react with hydroxide groups.

Furthermore, use of a linear or branched secondary alcohol as a starting material may result in a final, capped product offering improved handling, higher solubility and narrower gel range in water, better wetting power, and reduced foaming (forming more unstable foams), when compared with, for example, alkoxylated nonionic surfactants based on linear primary alcohols.

The methods used for the alkylene oxide capping may be any that are known to those skilled in the art. For example, in one embodiment, this reaction may be carried out at an elevated temperature or temperatures in a range from about 20° C. to about 180° C. In certain particular embodiments, the temperature may range from about 60° C. to about 160° C. Pressures from about 14 psig to about 60 psig may, in certain non-limiting embodiments, be employed, but other pressures may also be suitably efficacious. Those skilled in the art will be able to determine appropriate and/or optimized conditions and methodology upon, at most, routine experimentation.

In some non-limiting embodiments the capping alkoxylation may be carried out in the presence of an effective amount of a suitable alkaline catalyst, such as a hydroxide of an alkali metal or alkaline earth metal. A particularly convenient catalyst, in some non-limiting embodiments, is potassium hydroxide. The amount of alkaline catalyst may, in such embodiments, range from about 0.005 percent to about 1 percent by weight, based on the alcohol.

The final poly(alkylene oxide) capped poly(alkylene oxide)-extended linear or branched secondary alcohol of the invention may be used in formulations and compositions in any desired amount. However, it is commonly known to those skilled in the art that levels of surfactant in many conventional applications may range from about 0.05 to about 90 weight percent, more frequently from about 0.1 to about 30 weight percent, and in some uses from about 0.5 to about 20 weight percent, based on the total formulation. Those skilled in the art will be able to determine usage amounts via a combination of general knowledge of the applicable field as well as routine experimentation where needed.

Applications of the invention may include a wide variety of formulations and products. These include, but are not limited to, cleaners, detergents, hard surface cleaning formulations, polyurethanes, epoxies, thermoplastics, paints, coatings, metal products, agricultural products including herbicides and pesticides, oilfield and mining products, pulp and paper products, textiles, water treatment products, flooring products, inks, colorants, pharmaceuticals, cleaning products, personal care products, lubricants, and a combinations of these. In preparing these and other types of formulations and products, the poly(alkylene oxide) capped linear or branched secondary alcohol alkoxylate may contribute to or enhance a desirable property, such as surfactancy, detergency, wetting, re-wetting, foam reduction, additive stabilization, latex stabilization, drug delivery capability, emulsification, rinsing, plasticization, reactive dilution, rheology modification, suspension, pseudoplasticization, thickening, curing, impact modification, lubrication, emulsification and micro-emulsification, a combination thereof, or the like.

Examples of these applications include utility as surfactants in general; as low foam surfactants for household and commercial cleaning; as low foam surfactants in mechanical cleaning processes, as reactive diluents in casting, encapsulation, flooring, potting, adhesives, laminates, reinforced plastics, and filament windings; as coatings; as wetting agents; as rinse aids; as defoam/low foam agents; as spray cleaning agents; as emulsifiers for herbicides and pesticides; as metal cleaning agents; as suspension aids and emulsifiers for paints and coatings; as mixing enhancers in preparing microheterogeneous mixtures of organic compounds in polar and non-polar carrier fluids for agricultural spread and crop growth agents; as stabilizing agents for latexes; as microemulsifiers for pulp and paper products; and the like. In one non-limiting embodiment, compositions utilizing the alkoxylates may include microemulsions used for organic synthesis, formation of inorganic and organic particles, polymerization, and bio-organic processing and synthesis, as well as combinations thereof. In other non-limiting embodiments, the alkoxylates described herein may serve to dilute higher viscosity epoxy resins based on, for example, bisphenol-A, bisphenol-F, and novolak, as well as other thermoplastic and thermoset polymers, such as polyurethanes and acrylics. They may also find use in rheology modification of liquid systems such as inks, emulsions, paints, and pigment suspensions, where they may also be used to impart, for example, enhanced biodegradability, pseudoplasticity or thixotropic flow behavior. In these and other uses the alkoxylates may offer good and, in some cases, excellent performance, as well as relatively low cost.

The description hereinabove is intended to be general and is not intended to be inclusive of all possible embodiments of the invention. Similarly, the examples hereinbelow are provided to be illustrative only and are not intended to define or limit the invention in any way. Furthermore, those skilled in the art will be fully aware that other embodiments within the scope of the claims will be apparent, from consideration of the specification and/or practice of the invention as disclosed herein. Such other embodiments may include selections of specific alcohols, catalysts, and combinations of such compounds; proportions of such compounds; mixing and reaction conditions, vessels, and protocols; performance and selectivity; additional applications of the products not specifically addressed herein; and the like; and those skilled in the art will recognize that such may be varied within the scope of the claims appended hereto.

EXAMPLES

Example 1

About 2,971 g of an ethoxylated C12-C15 linear secondary alcohol, with an average of 9 moles of ethylene oxide (TERGITOL™ 15-S-9), is charged into an autoclave with about 7.17 g of potassium hydroxide as an alkoxylation catalyst. (TERGITOL is a trademark of The Dow Chemical Company.) After dehydration at 125° C. to about 267 ppm water, about 575 g (corresponding to about 1.5 moles) of butylene oxide is gassed in continuously with stirring. The reaction is carried out at the same temperature for about 15 hours, to completion. After cooling to approximately 70° C., the reaction product is then neutralized with about 6.94 g of acetic acid to give about 3208 g of a butylene oxide-capped, linear secondary alcohol alkoxylate, which is termed as "C12-15 Secondary Alcohol+9EO+1.5BO."

Example 2

About 3,563 g of an ethoxylated C12-C15 linear secondary alcohol, with an average of 9 moles of ethylene oxide (TERGITOL™ 15-S-9), is charged into an autoclave with about 9.03 g of potassium hydroxide as an alkoxylation catalyst. After dehydration at 125° C. to about 129.6 ppm water, about 695 g (corresponding to about 2 moles) of propylene oxide is gassed in continuously with stirring. The reaction is carried to completion at the same temperature for about 4 hours. The reaction is then neutralized with about 9.02 g of acetic acid to give about 3974 g of a propylene oxide-capped, linear secondary alcohol alkoxylate, which is termed as "C12-15 Secondary Alcohol+9EO+2PO."

Example 3

A product termed as "C12-15 Secondary Alcohol+9EO+ 2BO" is prepared as in Example 1, except that 1,732 grams of Tergitol™ 15-S-9, 3.70 grams potassium hydroxide, 420 grams of butylene oxide, and 3.74 grams acetic acid are used to result in 2,033 grams of product.

Example 4

A product termed as "C12-15 Secondary Alcohol+9EO+ 2.5BO" is prepared as in Example 1, except that 1,719 grams of Tergitol™ 15-S-9, 2.68 grams of potassium hydroxide, 520 grams butylene oxide, and 3.8 grams of acetic acid are used to result in 2,111 grams of product.

Example 5

A product termed as "C12-15 Secondary Alcohol+9EO+ 5PO" is prepared as in Example 1, except that 1,978 grams of Tergitol™ 15-S-9, 4.50 grams potassium hydroxide, 960 grams of propylene oxide, and 5.0 grams acetic acid are used to result in 2,685 grams of product.

Example 6

Comparative

The products prepared in Examples 1-5 are evaluated in comparison with TERGITOL™ 15-S-9 (C12-15 with 9 moles of ethylene oxide). An additional example composition, described as C12-15 with 12 moles of ethylene oxide for the initial alkoxylation reaction, or reactions, and 1.5 moles of butylene oxide for capping, is also evaluated. For this, the cloud point, the foaming property, surface tension and critical micelle concentration (CMC), dynamic surface tension, wetting property, and stability on caustic are studied.

The cloud point is determined in a 1 weight percent aqueous solution on METTLER™ FP90/81C automated cloud point instrument at a temperature increase rate of 3° C. per minute.

A Ross-Miles foaming test is carried out according to American Society for Testing Materials (ASTM) test D1173 on a 0.1 weight percent aqueous solution at 25° C. For this test the initial foam height and the foam heights at 1, 2, 3, 4 and 5 minutes are recorded.

Surface tension and CMC data were obtained using a KRÜSS™ Tensiometer K100 at 25° C. in water. For this test the surface tension of a surfactant-water solution is measured while incrementally adding the surfactant to de-ionized water. Results are measured in terms of dyne/centimeters using a Wilhelmy plate. Results are recorded versus surfactant concentration. The Critical Micelle Concentration is the point at which an increase in surfactant concentration no longer results in a change in surface tension.

Dynamic surface tension is measured with a KRÜSS™ BP2 Bubble Pressure Tensiometer for a 0.1 weight percent aqueous solution at 25° C.

Draves Wetting (skein wetting) property is tested following the procedure of ASTM D2281.

The biodegradability was determined by exposing the test compounds to microorganisms derived from activated sludge obtained from a municipal sewage treatment plant under aerobic static exposure conditions, using standard OECD 301 F methodology. OECD 301 F refers to the Organisation for Economic Cooperation and Development Guidelines for the Testing of Chemicals, "Ready Biodegradability: Manometric Respirometry Test," Procedure 301 F, adopted 17 Jul. 1992, which is incorporated herein by reference in its entirety.

The results of all tests are summarized in Table 1. It is seen that the examples of the invention have reduced foam at 5 minutes relative to propylene oxide capped or uncapped secondary alcohol ethoxylates.

TABLE 1

| Example | Cloud Point (° C.) | Ross-Miles Foam (mm)* | | | Surface Tension (mN/m)# | CMC (ppm)& | Dynamic Surface Tension (mN/m)† | Draves Wetting Time (sec.)‡ | Biodegradability |
|---|---|---|---|---|---|---|---|---|---|
| | | Initial | 1 min. | 5 min. | | | | | |
| $C_{12-15}$ + 9EO (TERGITOL 15-S-9 comparative example) | 59.0 | 128 | 120 | 100 | 29.5 | 50.0 | 39.4 | 6.8 | >60% |
| $C_{12-15}$ + 9EO + 1.5BO (Example 1) | 33.1 | 86 | 40 | 10 | 29.5 | 45.0 | 35.6 | 4.7 | >60% |
| $C_{12-15}$ + 9EO + 2PO (Example 2) | 51.4 | 120 | 102 | 42 | — | — | 37.6 | 7.0 | — |
| $C_{12-15}$ + 9EO + 2BO (Example 3) | 26.8 | 26 | 10 | 5 | — | — | 38.6 | 7.7 | — |
| $C_{12-15}$ + 9EO + 2.5BO (Example 4) | 22.5 | 14 | 7 | 4 | — | — | 43.1 | 25.1 | 67% |
| $C_{12-15}$ + 12EO + 1.5BO (additional example) | 45.9 | 98 | 84 | 7 | 30.9 | 49.7 | 37.6 | 9.4 | 68% |
| C12-15 + 9EO + 5PO (example 5) | 35.8 | 97 | 10 | 5 | 30.6 | 66.2 | 35.7 | 5.6 | — |

— No data available.
*0.1 wt % aqueous solution at 25° C.
0.05 wt % aqueous solution at 25° C.
&At 25° C.
†0.1 wt % aqueous solution at 25° C. and 4 bubbles/second.
‡0.1 wt % aqueous solution at 25° C.

To evaluate the stability of the samples on caustic, about 10 g of a surfactant sample is charged into a 22 ml sample vial containing about 1.0 g of sodium hydroxide beads. The sample vial is capped and wrapped with aluminum foil to protect the sample from light. The sample is then shaken continuously on an orbital shaker at about 150 rpm at 60° C. The color of the samples is compared after 5 days. After 10 days, samples are taken for a Ross-Miles foaming comparison (0.1 weight percent aqueous solution at 25° C.). The results are summarized in Table 2. It is seen that examples of the instant invention have a much higher color stability, as indicated by a lighter color after 5 days, relative to propylene oxide capped secondary alcohol ethoxylates, or uncapped secondary alcohol ethoxylates.

TABLE 2

|  | Color on 0 day | Color on 5th day | Original Sample Ross-Miles Foam | | | After 10 days Ross-Miles Foam | | |
| --- | --- | --- | --- | --- | --- | --- | --- | --- |
|  |  |  | Initial | 1 min. | 5 min | Initial | 1 min. | 5 min. |
| $C_{12-15}$ + 9EO (TERGITOL 15-S-9 comparative example) | Colorless | Deep Dark | 128 | 120 | 100 | 127 | 126 | 122 |
| $C_{12-15}$ + 9EO + 1.5BO (Example 1) | Slightly Yellow | Yellow | 86 | 40 | 10 | 90 | 22 | 7 |
| $C_{12-15}$ + 9EO + 2PO (Example 2) | Slightly Yellow | Light brown | 120 | 102 | 42 | 122 | 117 | 47 |

Example 7

Comparative

The secondary alcohol based C12-15+9EO+1.5BO prepared in Example 1 is compared with a linear alcohol based butylene oxide-capped product, PLURAFAC™ LF-221. (PLURAFAC is a trademark of BASF.) PLURAFAC™ LF-221 is a linear alcohol based C13-15+8.3EO+1.5BO. The comparison shows that the dynamic surface tension is more significantly reduced in the presence of the butylene oxide capped secondary alcohol ethoxylate than it is in the presence of a butylene oxide capped linear primary alcohol ethoxylate. This comparison is graphically illustrated in FIG. 1.

What is claimed is:

1. A composition of matter of the formula

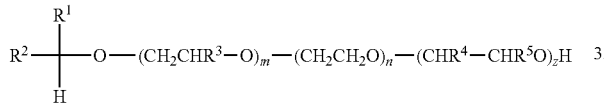

wherein $R^1$ and $R^2$ are each independently hydrogen or a linear or branched alkyl group containing from 1 to about 18 carbon atoms, provided that $R^1$ and $R^2$ together contain from about 8 to about 18 carbon atoms, and further provided that less than about 10 mole percent of $R^1$ or $R^2$ is hydrogen; $R^4$ and $R^5$ are each independently hydrogen or an alkyl radical containing 2 carbon atoms; n is an average value ranging from about 3 to about 40; and z is an average value ranging from 0.5 to 3.5, and wherein $R^4$ and $R^5$ together contain 2 carbon atoms.

2. The composition of claim 1 wherein $R^1$ and $R^2$ are each independently hydrogen or a linear or branched alkyl group containing from 1 to about 15 carbon atoms and $R^1$ and $R^2$ together contain from about 8 to about 16 carbon atoms.

3. The composition of claim 2 wherein $R^1$ and $R^2$ are each independently hydrogen or a linear or branched alkyl group containing from 1 to about 14 carbon atoms and $R^1$ and $R^2$ together contain from about 11 to about 15 carbon atoms.

4. The composition of claim 1 wherein the composition is incorporated into a formulation, wherein it improves a property thereof selected from the group consisting of surfactancy, detergency, wetting, re-wetting, foam reduction, additive stabilization, latex stabilization, drug delivery capability, emulsification and micro-emulsification, rinsing, plasticization, reactive dilution, dynamic surface tension reduction rheology modification, reduced reaction rates of surfactant with hydroxyl-reactive species, suspension, pseudoplasticization, thickening, curing, impact modification, lubrication, and combinations thereof.

5. The composition of claim 4 wherein the formulation is selected from the group consisting of a polyurethane formulation, an epoxy formulation, a paint formulation, a coating formulation, a metal working formulation, an agricultural formulation, an oilfield formulation, a mining formulation, a pulp or paper formulation, a textile formulation, a water treatment formulation, a flooring formulation, an ink formulation, a colorant formulation, a pharmaceutical formulation, a cleaning formulation, an agricultural crop formulation, a lubricant formulation, a personal care product formulation, a latex formulation, an emulsion polymerization formulation, a suspension polymerization formulation, an emulsification process formulation, a suspension process formulation, a dispersion process formulation, and combinations thereof.

6. A method of preparing a surfactant composition, comprising reacting a linear or branched secondary alcohol with at least one first alkylene oxide under reaction conditions sufficient to form an alkoxylated linear or branched secondary alcohol, and capping the alkoxylated linear or branched secondary alcohol with a second alkylene oxide under reaction conditions sufficient to form a composition of the formula:

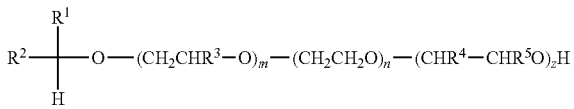

wherein $R^1$ and $R^2$ are each independently hydrogen or a linear or branched alkyl group containing from 1 to about 18 carbon atoms, provided that $R^1$ and $R^2$ together contain from about 8 to about 18 carbon atoms, and further provided that less than about 10 mole percent of $R^1$ or $R^2$ is hydrogen; $R^4$ and $R^5$ are each independently hydrogen or an alkyl radical containing 2 carbon atoms; n is an average value ranging from about 3 to about 40; and z is an average value ranging from 0.5 to 3.5, and wherein $R^4$ and $R^5$ together contain 2 carbon atoms.

7. The method of claim 6 wherein the linear or branched secondary alcohol is selected from the group consisting of: 2-decanol, 3-decanol, 4-decanol, 5-decanol, 2-undecanol, 3-undecanol, 4-undecanol, 5-undecanol, 2-dodecanol, 3-dodecanol, 4-dodecanol, 5-dodecanol, 6-dodecanol, 2-tridecanol, 3-tridecanol, 4-tridecanol, 5-tridecanol, 6-tridecanol, 2-tetradecanol, 3-tetradecanol, 4-tetra-decanol, 5-tetradecanol, 6-tetradecanol, 7-tetradecanol, 2-pentadecanol, 3-pentadecanol, 4-pentadecanol, 5-pentadecanol, 6-pentadecanol, 7-penta-decanol, 2-hexadecanol, 3-hexadecanol, 4-hexadecanol, 5-hexadecanol, 6-hexadecanol, 7-hexadecanol, and 8-hexadecanol; trimethyl nonanol; methyl-, ethyl-, propyl-, butyl-, hexyl-, heptyl-, octyl-, nonyl-, and decyl-branched secondary alcohols; secondary alcohols derived from hyrolysis of tripropylene, tetrapropylene, dibutylene, tributylene, and dihexene; and combinations thereof.

8. The method of claim 6 wherein n ranges from about 3 to about 30.

9. The method of claim 6 wherein the alkoxylated linear or branched secondary alcohol has a molecular weight from about 300 to about 1400.

10. The method of claim 6 wherein the at least one first alkylene oxide is reacted with the linear or branched secondary alcohol, and the alkoxylated linear or branched secondary alcohol is capped with the second alkylene oxide, under reaction conditions including a temperature ranging from about 20° C. to about 180° C. and a pressure from about 14 psig to about 60 psig.

11. The method of claim 6 wherein $R^1$ and $R^2$ are each independently hydrogen or a linear or branched alkyl group containing from 1 to about 15 carbon atoms and $R^1$ and $R^2$ together contain from about 8 to about 16 carbon atoms.

12. The method of claim 6 wherein up to about 10 mole percent of one or more primary alcohols having carbon chain lengths ranging from about C10 to about C16 are included with the secondary alcohols.

13. The method of claim 12 wherein the primary alcohol is selected from 1-decanol, 1-undecanol, 1-dodecanol, 1-tridecanol, 1-tetradecanol, 1-pentadecanol, 1-hexadecanol, and mixtures of two or more thereof.

14. The composition of claim 1 wherein $R^1$ and $R^2$ are each independently a linear or branched alkyl group containing from 1 to about 18 carbon atoms.

15. The method of claim 6 wherein $R^1$ and $R^2$ are each independently a linear or branched alkyl group containing from 1 to about 18 carbon atoms.

\* \* \* \* \*